(12) United States Patent
Garst et al.

(10) Patent No.: US 7,579,481 B2
(45) Date of Patent: Aug. 25, 2009

(54) METHOD OF MAKING IMIDAZOLE-2-ONES AND 2-THIONES

(75) Inventors: Michael E. Garst, Newport Beach, CA (US); Lloyd Dolby, Eugene, OR (US); Shervin Esfandiari, Eugene, OR (US)

(73) Assignee: Allergan, Inc., Irvine, CA (US)

( * ) Notice: Subject to any disclaimer, the term of this patent is extended or adjusted under 35 U.S.C. 154(b) by 391 days.

(21) Appl. No.: 11/467,292

(22) Filed: Aug. 25, 2006

(65) Prior Publication Data

US 2007/0197795 A1    Aug. 23, 2007

Related U.S. Application Data

(60) Provisional application No. 60/711,877, filed on Aug. 26, 2005.

(51) Int. Cl.
*A61K 31/4166* (2006.01)
*C07D 233/32* (2006.01)

(52) U.S. Cl. .............. 548/316.4; 548/335.1; 548/347.1; 514/392; 514/396; 514/401

(58) Field of Classification Search .............. 548/316.4, 548/335.1, 347.1; 514/392, 396, 401
See application file for complete search history.

(56) References Cited

OTHER PUBLICATIONS

Alker, et al., Long-Acting dihydropyridine calcium Antagonists. 5. Synthesis and structure-activity relationships for a series of 2-[[N-substituted-heterocyclyl) ethoxy] met hyl]-I,4dihydropyridine calcium antagonists, Journal of Medicinal Chemistry, vol. 33, 1990, pp. 1805-1811.*
Alker, et al., Long-Acting dihydropyridine calcium Antagonists. 5. Synthesis and structure-activity relationships for a series of 2-[[N-substituted-heterocyclyl) ethoxy] met hyl]-1,4dihydropyridine calcium antagonists, Journal of Medicinal Chemistry, vol. 33, 1990, pp. 1805-1811, XP0024136262.

* cited by examiner

*Primary Examiner*—Rei-Tsang Shiao
*Assistant Examiner*—Janet L Coppins
(74) *Attorney, Agent, or Firm*—Allergan, Inc.; Kevin Forrestal

(57) ABSTRACT

A method of 4-substituted imidazole-2-ones and thiones which comprises reacting a methylene urea or methylene thiourea wherein said methylene is substituted with the 4-subsituent and a cyano or alkycarboxylate group to provide said 4-substituted imidazole 2-one or thione.

10 Claims, No Drawings

METHOD OF MAKING IMIDAZOLE-2-ONES AND 2-THIONES

CROSS REFERENCE TO RELATED APPLICATIONS

This application is based on, and claims the benefit of, U.S. Provisional Application No. 60/711,877, filed Aug. 26, 2005, and which is incorporated herein by reference.

BACKGROUND OF THE INVENTION

1. Field of the Invention

A method of making 4-substituted imidazole-2-ones or thiones which comprises reacting a methylene urea or methylene thiourea wherein said methylene is substituted with the 4 subsituent and a cyano or alkycarboxylate group to provide said 4-substituted imidazole-2-one or thione.

2. Description of the Related Art

Compounds such as imidazole-2-ones and imidazole-2-thiones are useful as pharmaceutical compounds or as intermediates for preparing pharmaceutical compounds. Therefore, new and improved methods for making such compounds are continuously being developed.

BRIEF SUMMARY OF THE INVENTION

The present invention provides a method of preparing 4-substituted imidazole-2-ones and thiones which comprises reacting a methylene urea or methylene thiourea wherein said methylene is substituted with the 4-subsituent and a cyano or alkycarboxylate group to provide said 4-substituted imidazole 2-one or thione.

The above method may be carried out by reducing said methylene urea or methylene thiourea to said 4-substituted imidazole-2-one or thione.

Preferably, said methylene urea or methylene thiourea is reduced in the presence of a dialkyl aluminum hydride, e.g. diisobutylaluminum hydride (DIBAL-H).

Said methylene urea or methylene thiourea may be provided by reacting the corresponding 1-cyano, 1-amino, 1-substituted methane with a cyanate or a thiocyanate, e.g. potassium cyanate or potassium thiocyanate.

The reaction may be carried out in the liquid phase in the presence of an inert solvent at a temperature of less than 0° C. For example, said reaction may be carried out in a dichloromethane solvent.

Preferably, said 4-substituent is selected form the group consisting of alkyl, aryl and alkylaryl radicals which have from 1 to 50 carbon atoms which radicals may be substituted with halogen, nitrogen, oxygen, sulfur and phosphorus substituents.

More preferably said 4-substituent is benzyl.

DETAILED DESCRIPTION OF THE INVENTION

The method of the present invention may be carried out in accordance with the schemes below.

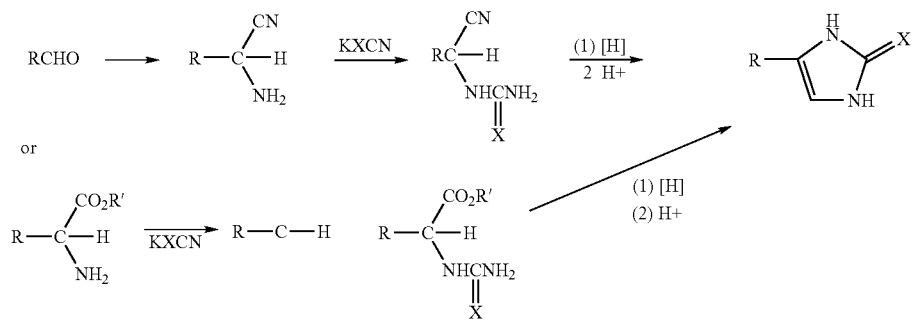

In the above schemes, R is selected from the group consisting of alkyl, aryl and alkyl aryl radicals having from 1 to 50 carbon atoms which radicals may be substituted with halogen, nitrogen, oxygen, sulfur and phosphorus substituents, R' is a lower alkyl having from 1 to 6 carbon atoms, and X is O or S.

The invention is further illustrated by the following examples which are illustrative of a specific mode of practicing the invention and are not intended as limiting the scope of the claims.

EXAMPLE 1

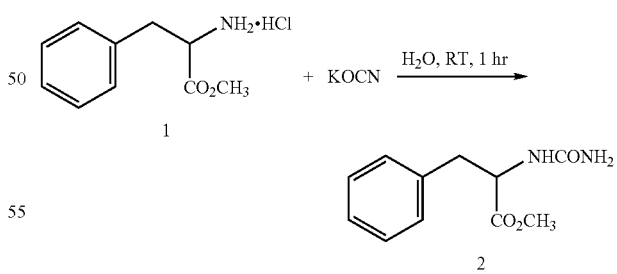

Methyl 2-(aminocarbonylamino)-3-phenylpropanoate, 2. A 500 mL 3-necked flask equipped with a mechanical stirrer was charged with L-phenylalanine methyl ester hydrochloride 1 (24.8 g, 0.115 mol) in water (100 mL). Potassium cyanate (9.5 g, 0.117 mol) was added. After stirring for 1 hr at room temperature, the white solid was collected and air dried to give 19.5 g (76%) of methyl 2-(aminocarbonylamino)-3-phenylpropanoate (2). HPLC analysis showed a purity of 99%. $^1$H NMR (CDCl$_3$) δ 7.5 (s, 5 h), 6.5 (d, 1H), 5.3 (s, 2H), 4.8 (dd, 1H), 3.75 (s, 3H), 3.1 (d, 2H).

EXAMPLE 2

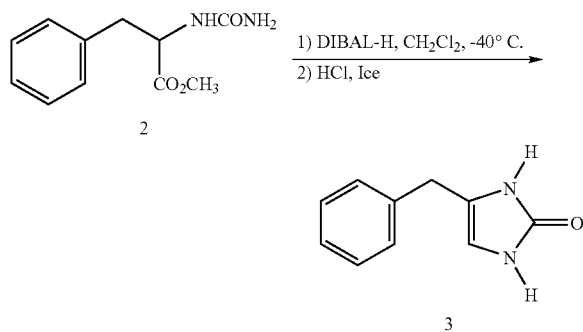

4-Benzylimidazolin-2-one, 3. A 250 mL 3-necked flask equipped with a dropping funnel, a thermometer and a stirbar, was charged with urea methyl ester 2 (6.66 g, 0.03 mol) in dichloromethane (30 mL) under argon. The resulting solution cooled to −40° C. A solution of diisobutylaluminum hydride (0.066 mol, 66 mL of 1 M solution in dichloromethane) was slowly added over a period of 45 min. During this addition the internal temperature rose to −30° C. and then fell to −40° C. After 15 min, HPLC analysis of an aliquot worked up in 3 M hydrochloric acid showed complete consumption of starting material. The reaction mixture was transferred by a cannula into a vigorously stirring mixture of conc. HCl (25 mL) and crushed ice (75 g). The product slowly precipitated while stirring the resultant mixture at room temperature for 5 hr. The white solid was collected and air dried to give 2.2 g (42%) of 4-benzylimidazolin-2-one (3). HPLC analysis showed a purity of >97%. $^1$H NMR (warm d$_6$-DMSO) 67 10.0 (br s, 1H), 9.7 (br s, 1H), 7.3 (s, 5H), 6.0 (s, 1H), 3.6 (s, water peak), 3.5 (s, 2H).

HPLC analysis: column: Alltech Alltima, C$_{18}$, 5μ, 250×4.6 mm, flow 1 mL/min, at 40° C.; wavelength 210 nm. Condition: H$_2$O/A1/CH$_3$OH (25/10/65). The retention time for 1 was 2.7 min, for 2 3.7 min and for 3, 3.9 min. A1 is made of 700 mL water, 300 mL methanol, 3 mL triethylamine and enough phosphoric acid to give a pH of 3.4.

While particular embodiments of the invention have been described it will be understood of course that the invention is not limited thereto since many obvious modifications can be made and it is intended to include within this invention any such modifications as will fall within the scope of the appended claims.

The invention claimed is:

1. A method of making 4-substituted imidazole-2-ones and imidazole-2-thiones which comprises reacting a methylene urea or methylene thiourea bearing the 4-subsituent with a cyano or alkycarboxylate group, thereby providing said 4-substituted imidazole 2-one or thione.

2. The method of claim 1 wherein said 4-substituted imidazole-2-one or thione is provided by reducing said methylene urea or methylene thiourea.

3. The method of claim 2 wherein said methylene urea or methylene thiourea is reduced in the presence of a dialkyl aluminum hydride.

4. The method of claim 3 wherein said dialkyl aluminum hydride is diisobutyl aluminum hydride.

5. The method of claim 4 wherein said methylene urea or methylene thiourea is provided by reacting a 1-cyano, 1-amino, or 1-substituted methane with a cyanate or a thiocyanate.

6. The method of claim 5 wherein said cyanate is potassium cyanate and said thiocyanate is potassium thiocyanate.

7. The method of claim 1 wherein said reaction is carried out in the liquid phase at a temperature of less than 0° C.

8. The method of claim 7 wherein said reaction is carried out in a dichloromethane solvent.

9. The method of claim 1 wherein said 4-substituent is selected form the group consisting of alkyl, aryl and alkylaryl radicals which have from 1 to 50 carbon atoms which radicals may be substituted with halogen, nitrogen, oxygen, sulfur and phosphorus substituents.

10. The method of claim 9 wherein said 4-substituent is benzyl.

* * * * *